US008906345B2

(12) United States Patent
Anthony et al.

(10) Patent No.: US 8,906,345 B2
(45) Date of Patent: Dec. 9, 2014

(54) MULTIMERIC PARTICLES (75) Inventors: Daniel Anthony, Oxford (GB);
Benjamin Guy Davis, Oxford (GB);
Nicola Sibson, Oxford (GB)

(73) Assignee: Isis Innovation Limited, Oxford (GB)

( * ) Notice: Subject to any disclaimer, the term of this patent is extended or adjusted under 35 U.S.C. 154(b) by 1266 days.

(21) Appl. No.: 12/442,100

(22) PCT Filed: Sep. 20, 2007

(86) PCT No.: PCT/GB2007/003557
§ 371 (c)(1),
(2), (4) Date: Nov. 13, 2009

(87) PCT Pub. No.: WO2008/035069
PCT Pub. Date: Mar. 27, 2008

(65) Prior Publication Data
US 2010/0092394 A1 Apr. 15, 2010

(30) Foreign Application Priority Data
Sep. 20, 2006 (GB) .................................. 0618524.3

(51) Int. Cl.
A61B 5/055 (2006.01)
A61K 49/00 (2006.01)
A61K 49/18 (2006.01)
A61K 47/48 (2006.01)

(52) U.S. Cl.
CPC ....... A61K 47/48338 (2013.01); A61K 49/0004 (2013.01); A61K 49/1887 (2013.01)
USPC .......... 424/9.323; 424/1.29; 424/9.1; 424/9.3; 424/9.32

(58) Field of Classification Search
CPC ........... A61K 2123/00; A61K 2121/00; A61K 51/0478; A61K 51/04; A61K 51/1217; A61K 49/06; A61K 49/085; A61K 49/1806; A61K 49/128; A61K 49/12; A61K 49/00; A61K 49/004; A61K 49/0002; A61K 49/001; A61K 49/0017; A61K 49/08; A61K 49/10; A61K 49/101; A61K 49/18; A61K 51/00; A61K 51/02; A61K 51/06; A61K 51/12; A61K 9/00; A61K 9/08; A61K 9/10; A61K 9/14; A61K 49/0004; A61K 49/1821; A61K 49/1824; A61K 49/1827; A61K 49/1818; A61K 49/1833; A61K 49/1851; A61K 49/1887; A61K 47/48338; B82Y 5/00; A61B 5/055; A61B 5/04; A61B 5/05; A61B 5/053
USPC ............ 424/1.11, 1.49, 1.65, 1.69, 1.73, 9.1, 424/9.3, 9.32, 9.322, 9.323, 9.34, 9.341, 424/9.35, 9.351, 9.36, 9.4, 9.5, 9.6, 9.7, 9.8, 424/1.29, 1.33, 1.37, 400
See application file for complete search history.

(56) References Cited

U.S. PATENT DOCUMENTS

| 4,698,302 | A | 10/1987 | Whitehead et al. | |
|---|---|---|---|---|
| 5,352,432 | A | 10/1994 | Menz et al. | |
| 5,427,567 | A | 6/1995 | Adcock | |
| 5,582,172 | A | 12/1996 | Papisov et al. | |
| 6,274,121 | B1 | 8/2001 | Pilgrimm | |
| 6,511,967 | B1 | 1/2003 | Weissleder et al. | |
| 7,829,350 | B2 * | 11/2010 | Josephson et al. | ............ 436/526 |
| 2008/0311048 | A1 | 12/2008 | Davis et al. | |

FOREIGN PATENT DOCUMENTS

| DE | 198 20 847 A1 | 11/1999 |
|---|---|---|
| EP | 0 156 537 A2 | 10/1985 |
| EP | 0 156 537 A3 | 10/1985 |
| EP | 0 260 098 A2 | 3/1988 |
| EP | 0 260 098 A3 | 3/1988 |
| WO | WO 90/01295 A1 | 2/1990 |
| WO | WO 90/03401 A1 | 4/1990 |
| WO | WO 93/14142 A1 | 7/1993 |
| WO | WO 96/40273 A2 | 12/1996 |
| WO | WO 96/40273 A3 | 12/1996 |
| WO | WO 98/23293 A1 | 6/1998 |
| WO | WO 98/56752 A1 | 12/1998 |
| WO | WO 00/08038 A2 | 2/2000 |
| WO | WO 00/08038 A3 | 2/2000 |
| WO | WO 02/46241 A2 | 6/2002 |
| WO | WO 02/46241 A3 | 6/2002 |
| WO | WO 02/098364 | * 12/2002 |
| WO | WO 02/098364 A2 | 12/2002 |
| WO | WO 02/098364 A3 | 12/2002 |
| WO | WO 2004/087160 A1 | 10/2004 |
| WO | WO 2005/061724 A1 | 7/2005 |
| WO | WO 2007/020450 A2 | 2/2007 |
| WO | WO 2007/020450 A3 | 2/2007 |
| WO | WO 2007/063300 A2 | 6/2007 |
| WO | WO 2007/063300 A3 | 6/2007 |
| WO | WO 2007/092909 A2 | 8/2007 |
| WO | WO 2007/092909 A3 | 8/2007 |

OTHER PUBLICATIONS

Bhatia, S.K. et al., "The State Diagram for Cell Adhesion Mediated by Two Receptors," *Biophysical Journal*, Apr. 2003, vol. 84, pp. 2671-2690.

Bock, K. et al., "Conformations in Solution of $\alpha,\alpha$-Trehalose, $\alpha$-D-Glucopyranosyl $\alpha$-D-Mannopyranoside, and Their 1-Thioglycosyl Analogs, and a Tentative Correlation of Their Behaviour with Respect to the Enzyme Trehalase," *Eur. J. Biochem.*, 1983, vol. 131, pp. 595-600.

Botnar, R.M. et al., "In Vivo Magnetic Resonance Imaging of Coronary Thrombosis Using a Fibrin-Binding Molecular Magnetic Resonance Contrast Agent," *Circulation*, Sep. 14, 2004, vol. 110, pp. 1463-1466.

(Continued)

*Primary Examiner* — D L Jones
(74) *Attorney, Agent, or Firm* — Kilpatrick Townsend & Stockton LLP (57) ABSTRACT

The invention provides multimeric particle comprising metal-containing particles covalently bonded to one another by linker groups wherein at least some of said linker groups are cleavable. The invention further provides a contrast agent comprising said multimeric particles, along with a method of improving contrast of an image using said contrast agent.

11 Claims, 6 Drawing Sheets

(56) References Cited

OTHER PUBLICATIONS

Briley-Saebo, K. et al., "Hepatic cellular distribution and degradation of iron oxide nanoparticles following single intravenous injection in rats: implications for magnetic resonance imaging," *Cell Tissue Res.*, 2004, vol. 316, pp. 315-323.

Brunk, D.K. et al., "Sialyl Lewis$^x$/E-Selectin-Mediated Rolling in a Cell-Free System," *Biophysical Journal*, Nov. 1996, vol. 71, pp. 2902-2907.

Bulte, J.W.M. et al., "Iron oxide MR contrast agents for molecular and cellular imaging," *NMF in Biomedicine*, 2004, vol. 17, pp. 484-499.

Chen, H.H. et al., "MR Imaging of Biodegradable Polymeric Microparticles: A Potential Method of Monitoring Local Drug Delivery," *Magnetic Resonance in Medicine*, 2005, vol. 53, pp. 614-620.

Choudhury, R.P. et al., "Molecular, Cellular and Functional Imaging of Atherothrombosis," *Nature Reviews*, Nov. 2004, vol. 3, pp. 913-925.

Choudhury, R.P. et al., "MRI and Characterization of Atherosclerotic Plaque: Emerging Applications and Molecular Imaging," *Arteriosclerosis, Thrombosis, and Vascular Biology*, Jul. 2002, vol. 22, pp. 1065-1074.

Cybulsky, M.I. et al., "A major role for VCAM-1, but not ICAM-1, in early atherosclerosis," *The Journal of Clinical Investigation*, May 2001, vol. 107, No. 10, pp. 1255-1262.

Dunning, M.D. et al., "Magnetic resonance imaging of functional Schwann cell transplants labeled with magnetic microspheres," *NeuroImage*, 2006, vol. 31, pp. 172-180.

Eisele, T. et al., "Synthesis of a thio-linked Lewis A (Le$^a$) epitope," *Carbohydrate Research*, 1998, vol. 306, pp. 81-91.

Eniola, A.O. et al., "Interplay between Rolling and Firm Adhesion Elucidated with a Cell-Free System Engineered with Two Distinct Receptor-Ligand Pairs," *Biophysical Journal*, Oct. 2003, vol. 85, pp. 2720-2731.

Heebøll-Nielsen. A. et al., "Superparmagnetic Adsorbents for High-Gradient Magnetic Fishing of Lectins out of Legume Extracts," *Biotechnology and Bioengineering*, Aug. 5, 2004, vol. 87, No. 3, pp. 311-323.

Horisberger, M., "Immobilization of protein and Polysaccharide on Magnetic Particles: Selective Binding of Microorganisms by Concanavalin A-Magnetite," *Biotechnology and Bioengineering*, 1976, vol. XVII, pp. 1647-1651.

Iiyama, K. et al., "Patterns of Vascular Cell Adhesion Molecule-1 and Intercellular Adhesion Molecule-1 Expression in Rabbit and Mouse Atherosclerotic Lesions and at Sites Predisposed to Lesion Formation," *Circulation Research*, Jul. 23, 1999, vol. 85, pp. 199-207.

International Search Report mailed on Mar. 6, 2008, for International Application No. PCT/GB2007/003557, filed on Sep. 20, 2007, 4 pages.

Jaffer, F.A. et al., "Molecular and Cellular Imaging of atherosclerosis, Emerging Applications," *Journal of the American College of Cardiology*, Apr. 4, 2006, vol. 47, No. 7, pp. 1328-1338.

Jaffer, F.A. et al., "Seeing Within: Molecular Imaging of the Cardiovascular System," *Circulation Research*, Mar. 5, 2004, vol. 94, pp. 433-445 and Online Data Supplement (7 pages).

Kelly, K.A. et al., "Detection of Vascular Adhesion Molecule-1 Expression Using a Novel Multimodal Nanoparticle," *Circulation Research*, Feb. 18, 2005, vol. 96, pp. 327-336 and Data Supplement (1 page).

Kooi, M.E. et al., "Accumulation of Ultrasmall Superparamagnetic Particles of Iron Oxide in Human Atherosclerotic Plaques Can Be Detected by In Vivo Magnetic Resonance Imaging," *Circulation*, May 20, 2003, vol. 107, pp. 2453-2458.

Laconte, L. et al., "Magnetic nanoparticle probes," *Nanotoday*, May 2005, pp. 32-38.

Lipinski, M.J. et al., "Technology Insight: targeting of biological molecules for evaluation of high-risk atherosclerotic plaques with magnetic resonance imaging," *Nature Clinical Procedure*, Nov. 2004, vol. 1, No. 1, pp. 48-55.

Louie, A.Y. et al., "in vivo visualization of gene expression using magnetic resonance imaging," *Nature Biotechnology*, Mar. 2000, vol. 18, pp. 321-325.

Mäntylä, T. et al., "Targeted Magnetic Resonance Imaging of Scavidin-Receptor in Human Umbilical Vein Endothelial Cells in Vitro," *Magnetic Resonance in Medicine*, 2006, vol. 55, pp. 800-804.

Morawski, A.M. et al., "Targeted contrast agents for magnetic resonance imaging and ultrasound," *Current Opinion in Biotechnology*, 2005, vol. 16, pp. 89-92.

Nakashima, Y. et al., "Upregulation of VCAM-1 and ICAM-1 at Atherosclerosis-Prone Sites on the Endothelium in the ApoE-Deficient Mouse," *Arteriosclerosis, Thrombosis, and Vascular Biology*, May 1998, vol. 18, pp. 842-851.

Pearce, O.M.T. et al., "Glycoviruses: Chemical Glycosylation Retargets Adenoviral Gene Transfer," *Angew. Chem. Int. Ed.*, 2005, vol. 44, pp. 1057-1061.

Pulfer, S.K. et al., "Enhanced Brain Tumor Selectivity of Cationic Magnetic Polysaccharide Microspheres," *Journal of Drug Targeting*, 1998, vol. 6, No. 3, pp. 215-227.

Ramos, C.L. et al., "Direct Demonstration of P-Selectin- and VCAM-1-Dependent Mononuclear Cell Rolling in Early Atherosclerotic Lesions of Apolipoprotein E-Deficient Mice," *Circular Research*, 1999, vol. 84, pp. 1237-1244.

Robinson, M.A. et al., "LEAPT: Lectin-directed enzyme-activated prodrug therapy," *PNAS*, Oct. 5, 2004, vol. 101, No. 40, pp. 14527-14532.

Rogers, W.J. et al., "Factors regulating macrophage endocytosis of nanoparticles: implications for targeted magnetic resonance plaque imaging," *Atherosclerosis*, 2005, vol. 178, pp. 67-73.

Rosi, N.L. et al., "Nanostructures in Biodiagnostics," *Chemical Reviews*, 2005, vol. 105, No. 4, pp. 1547-1562.

Rye, C.S. et al., "The synthesis of a novel thio-linked disaccharide of chondroitin as a potential inhibitor of polysaccharide lyases," *Carbohydrate Research*, 2004, vol. 339, pp. 699-703.

Saleh, A. et al., "Central nervous system inflammatory response after cerebral infarction as detected by magnetic resonance imaging," *NMR in Biomedicine*, 2004, vol. 17, pp. 163-169.

Saleh, A. et al., "In vivo MRI of brain inflammation in human ischaemic stroke," *Brain*, 2004, vol. 127, pp. 1670-1677.

Shapiro, E.M. et al., "MRI detection of single particles for cellular imaging," *PNAS*, Jul. 27, 2004, vol. 101, No. 30, pp. 10901-10906.

Sibson, N.R. et al., "MRI Detection of Early Endothelial Activation in Brain Inflammation," *Magnetic Resonance in Medicine*, 2004, vol. 51, pp. 248-252.

So, P-W. et al., "Generic Method for Imaging Transgene Expression," *Magnetic Resonance in Medicine*, 2005, vol. 54, pp. 218-221.

Stowell, C.P. et al., "Preparation of Neoglycoproteins Using 2-Imino-2-methoxyethyl 1-Thioglycosides," Chapter 19 in *Methods in Enzymology*, 1982, vol. 83, Academic Press, Inc., pp. 278-279.

Takada, M. et al., "The Cytokine-adhesion Molecule Cascade in Ischemia-Reperfusion Injury of the Rat Kidney," *J. Clin. Invest.*, 1997, vol. 99, pp. 2682-2690.

Tiefenauer, L.X. et al., "In Vivo Evaluation of Magnetite Nanoparticles for Use as a Tumor Contrast Agent in MRI," *Magnetic Resonance Imaging*, 1996, vol. 14, No. 4, pp. 391-402.

Valadon, P. et al., "Screening phage display libraries for organ-specific vascular immunotargeting in vivo," *PNAS*, Jan. 10, 2006, vol. 103, No. 2, pp. 407-412.

Weller, G.E.R. et al., "Targeted Ultrasound Contrast Agents: In Vitro Assessment of Endothelial Dysfunction and Multi-Targeting to ICAM-1 and Sialyl Lewis$^x$," *Biotechnology and Bioengineering*, Dec. 20, 2005, vol. 92, No. 6, pp. 780-788.

Wickline, S.A. et al., "Applications of Nanotechnology to Atherosclerosis, Thrombosis, and Vascular Biology," *Arteriosclerosis, Thrombosis, and Vascular Biology*, Mar. 2006, vol. 26, pp. 435-441.

Wickline, S.A. et al., "Molecular Imaging, Targeted Therapeutics, and Nanoscience," *Journal of Cellular Biochemistry Supplement*, 2002, vol. 39, pp. 90-97.

Winter, P.M. et al., "Molecular Imaging of Angiogenesis in Early-Stage Atherosclerosis With $\alpha_v\beta_3$-Integrin-Trageted Nanoparticles," *Circulation*, Nov. 4, 2003, vol. 108, pp. 2270-2274.

(56) References Cited

OTHER PUBLICATIONS

Wu, Y.L. et al., "In situ labeling of immune cells with iron oxide particles: An approach to detect organ rejection by cellular MRI," *PNAS*, Feb. 7, 2006, vol. 103, No. 6, pp. 1852-1857.

Wunderbaldinger, P. et al., "Crosslinked Iron Oxides (CLIO): A New Platform for the Development of Targeted MR Contrast Agents," *Academic Radiology*, 2002, vol. 9, Suppl. 2, pp. S304-S306.

* cited by examiner

MULTIMERIC PARTICLES

FIELD OF THE INVENTION

The invention is in the field of metal-containing multimeric particles, particularly for use in imaging applications.

DESCRIPTION OF THE PRIOR ART

A variety of imaging techniques are available for diagnostic purposes. Such imaging techniques are generally non invasive and include magnetic resonance imaging (MRI) and ultrasound. Contrast agents are used in imaging to increase the signal difference between the area of interest and background. Iron containing particles are know for use in molecular imaging applications. The superparamagnetic behaviour of mixed iron oxides (e.g. magnetite, $Fe_2O_3/Fe_3O_4$) results in magnetization when placed in a magnetic field such as is found in an MRI apparatus. Accordingly, iron oxide nanoparticles described as superparamagnetic iron oxide particles (SPIOs) were first used as magnetic resonance imaging (MRI) contrast agents some years ago, as described in LaConte et al, Nanotoday, May 2005, 32-28 and Bulte et al, NMR Biomed. 2004, 17, 484-499.

The size and coating of SPIOs helps to determine where the particles end up when administered to a patient. However, it is still difficult to accurately target SPIOs to a particular region of interest and more recent work has therefore focused on the use of targeting moieties. These targeting moieties include sugars, antibodies and other ligands which can be attached to the SPIOs in order to target the particles to a desired region.

Existing SPIOs of a number of different sizes have been prepared and tested. It has been found that small particles (of the order of 50 nm to 200 nm) provide a strong magnetic resonance signal, while larger particles (around 1 μm) provide a much better signal to noise ratio. However, both types of particles suffer from disadvantages. Small particles are often cleared quickly from the site of interest, but may linger in the blood. As a result, the quality of MRI scans is reduced owing to the low signal to background noise ratio. Large particles, on the other hand, can cause microvessel occlusion leading to a lower clearance rate and also the potential for new iatrogenic pathology.

There is thus a need to provide new particles which can be used as contrast agents (also known as imaging agents) which can be used in place of the particles discussed above.

SUMMARY OF THE INVENTION

It has now been found that a balance of properties can be achieved by multimeric particles which initially comprise a number of smaller particles, but which can subsequently be broken down into smaller constituent particles. This can achieve both good signal to noise ratio and biodegradability to prevent the dwell time of the particle from being of sufficient length to cause damage through occlusion that might lead to ischaemia.

Accordingly, the invention provides a multimeric particle comprising metal-containing particles covalently bonded to one another by linker groups wherein at least a portion of the linker groups are cleavable. Preferably the metal-containing particles comprise iron or iron oxide coated with a material which is covalently bonded to one or more linker groups. Preferably at least some of the linker groups are enzymatically cleavable or otherwise capable of being broken down in vivo.

The claimed multimeric particles allow for degradation following administration, and thus allow variation in the magnetic resonance image over time. When first administered, the multimeric particles, being larger in diameter than their constituent metal-containing particles, provide a high signal to noise ratio. However, the multimeric particles can be broken down due to cleaving of the cleavable linker groups, resulting in biodegradability of the multimeric particles, which improves safety.

The invention also provides a contrast agent comprising multimeric particles described above, along with the use of said multimeric particles as a contrast agent. The invention further provides said multimeric particles and said contrast agent use in a diagnostic method practised on the human or animal body, and the use of said multimeric particles in the manufacture of a contrast agent for use in medical imaging.

The invention also provides a method of imaging a region of a patient's body which comprises administering said contrast agent to the patient and recording a magnetic resonance image of the patient. There is also provided a method for enhancing the contrast of an image obtained by a medical imaging technique, which method comprises, prior to an image being formed, the administration of said contrast agent.

DESCRIPTION OF THE FIGURES

FIG. 1 is a schematic diagram illustrating the invention. It shows, in the first picture, starting materials (metal-containing particles) which are subsequently covalently bonded to one another by way of the linking groups (shown as straight lines in the second picture) to form the multimeric particles of the invention. These multimeric particles can be injected in vivo. Once in the body, the linker groups can be cleaved, resulting in degradation of the multimeric particles into smaller constituent parts (shown in the third picture).

DETAILED DESCRIPTION OF THE INVENTION

As used herein, an alkyl group or moiety is a linear or branched alkyl group or moiety preferably containing from 1 to 6 carbon atoms such as a $C_{1-4}$ alkyl group or moiety. Examples of $C_{1-4}$ alkyl groups and moieties include methyl, ethyl, n-propyl, i-propyl, n-butyl, i-butyl and t-butyl. For the avoidance of doubt, where two alkyl moieties are present in a group, the alkyl moieties may be the same or different.

As used herein the term amino represents a group of formula —$NH_2$. The term $C_{1-6}$ alkylamino represents a group of formula —NHR' wherein R' is a $C_{1-6}$ alkyl group, preferably a $C_{1-4}$ alkyl group, as defined previously. The term di($C_{1-6}$ alkyl)amino represents a group of formula —NR'R" wherein R' and R" are the same or different and represent $C_{1-6}$ alkyl groups, preferably $C_{1-4}$ alkyl groups, as defined previously. As used herein a $C_{1-6}$ acetylamino group is a $C_{1-6}$ acetyl group attached to an amino group as defined above. Similarly, a di($C_{1-6}$)acetylamino group is an acetyl group bearing two $C_{1-6}$ alkyl groups and attached to an amino group as defined above.

As used herein, an alkoxy group is typically a said alkyl group attached to an oxygen atom. Similarly, an alkylthio group is typically a said alkyl group attached to a thio group.

For the avoidance of doubt, as used herein a majority refers to more than 50% of a sample, and a minority refers to less than 50% of a sample.

As used herein, the term multimeric represents a structure of identical or different subunits which are covalently bonded together. The subunits in the invention are metal-containing particles.

Preferably the multimeric particles of the invention have magnetic properties, for example being magnetic, paramagnetic or superparamagnetic. The multimeric particles are preferably suitable for use in magnetic resonance imaging applications, particularly for MRI scanning, therefore paramagnetic and superparamagnetic particles are preferred, in particular superparamagnetic particles.

In another embodiment the multimeric particles may have other properties capable of being detected. For example, they may be luminescent, for example fluorescent or phosphorescent. Such particles would be useful in imaging applications where a change in luminescence is detectable.

The metal-containing particles will generally be from 1 nm to 200 nm in diameter, preferably from 1 to 100 nm, more preferably from 5 to 20 nm. Clearly when these particles are manufactured there will be a spread of particle diameters, therefore the range above refers to the average particle diameter. The average particle diameter can be determined as a root mean squared diameter, e.g. as measured by laser scattering. Usually a Brownian distribution of particle sizes will be obtained, of which the peak is considered the average particle diameter.

The resulting multimeric particles will generally be from 200 nm to 2 µm in diameter, more preferably from 500 nm to 1.5 µm in diameter, for example around 1 µm. As with the metal-containing particles, there will be a spread of diameters for the multimeric particles, with the ranges above referring to the average diameter. One multimeric particle will generally comprise around one million of the metal-containing particles; more preferably one multimeric particle will consist of around one million of the metal-containing particles.

In one embodiment, in order to obtain multimeric particles within a preferred size range, the metal-containing particles and linker groups can be reacted in quantities and under conditions such that much larger multimeric particles or aggregate particles are first obtained. These over-sized particles can then be physically broken down into multimeric particles of the correct size, for example by milling or pulverising (e.g. by mechanical sheer forces).

The metal-containing particles which form the multimeric particles may be the same or different. For example, the multimeric particles may comprise a number of different metal-containing particles (containing different metals and/or different coatings). Alternatively, the multimeric particles may comprise a single type of metal-containing particle, such that all metal-containing particles comprise the same metal and the same coating.

The metal-containing particles contain a central metal or metal oxide core. The metal or metal oxide core is at least partially covered with a coating which is covalently bonded to one or more linker groups. Preferably the metal or metal oxide core is completely covered by said coating. In order for the covalent bond to be formed, then prior to formation of the multimeric particle the coating must be functionalised in order to covalently bond to the linker groups.

Suitable cores include iron-containing colloidal particles. For example, suitable cores include those comprising iron hydroxide, iron oxide hydrate, iron (II) oxide, iron (III) oxide, mixed iron oxide, metallic iron or mixtures thereof. In mixed iron oxides other metal oxides such as oxides of cobalt, nickel, manganese, beryllium, magnesium, calcium, barium, strontium, copper, zinc, platinum, aluminium, chromium, bismuth, rare earth metals and mixtures thereof can be present. Preferably the core comprises an iron (II) or iron (III) oxide or an iron hydroxide or a mixture thereof. More preferably the core comprises iron oxide, in particular iron (III) oxide.

For applications where for example a luminescent property is required (e.g. luminescent probes, suitable particles include gold nanoparticles and cadmium sulphide particles (cadmium sulphide quantum dots).

The coatings include well-known materials which have been used in the past to coat metal particles such as SPIOs and CLIOs. Suitable materials include long-chain sugars and the like, for example dextran, carbodextran, mannan, cellulose and starch-based polymers. It is also possible to use materials such as dendrimers. Preferably the coating comprises dextran, more preferably the coating consists of dextran. Where possible, the coatings may comprise materials which are cross-linkable. However, it is preferred that the coating is not cross-linked.

The coatings either provide or can be pre-reacted in order to provide functionalisation capable of bonding to the linker groups. For example, a dextran coating can provide amine groups which are capable of being reacted with a linker group in a process for preparing the multimeric particles. Alternatively, a coating can be pre-reacted, prior to reaction with a linker group, to form a functional group which is capable of reacting with a linker group in a process for preparing the multimeric particles.

Prior to formation of the multimeric particles, each metal-containing particle, comprising a metal or metal oxide core covered with a coating as described above, contains at least one functional group capable of reacting with a linker group. Preferably each metal-containing particle will contain a number of such functional groups, allowing bonds to be formed with a number of linker groups.

The linker groups in the multimeric particles act both to bind the metal-containing particles together and to maintain distance between said metal-containing particles. The length of the linker group can thus be manipulated in order to achieve optimal separation of the multimeric particles.

At least a portion of the linker groups are cleavable, thus allowing the multimeric particles to be broken down into smaller particles. Depending on the structure of the multimeric particle, a different number of linker groups will need to be cleaved in order to cause breakdown of the multimeric particle. For example, if two clusters of metal-containing particles (each cluster comprising metal-containing particles covalently bonded by linker groups) are bonded to each other by a single linker groups, then only this single linker group will need to be cleaved in order to cause degradation of the multimeric particle. Thus, in a preferred embodiment, the portion of said linker groups which are cleavable is chosen such that it is sufficient to cause degradation of the multimeric particle. As used herein, degradation means breakdown of the multimeric particle into two or more constituent parts, these constituent parts being separate from one another, not being covalently bonded to one another).

More preferably the majority of the linker groups are cleavable, most preferably all of the linker groups are cleavable, thus allowing for the multimeric particles to be broken down into their constituent metal-containing particles. However, clearly the types of linker groups and their relative proportions can be chosen in order to manipulate both the length of time before degradation, and also the level of degradation which occurs. For example a portion of the linker groups could be chosen to be cleavable under certain conditions in vivo, with the remaining linker groups being chosen to be either non-cleavable in vivo, or cleavable under different conditions or on a much longer timescale. Thus, the degradation of the multimeric particles can be tuned according to the purpose for which the multimeric particles are to be used.

Preferably the linker groups are stable in a carrier substance in which the multimeric particles can be stored, but at least some are cleavable after administration into a sample. For example, the linker groups may be cleavable enzymatically, or cleavable by another mechanism in vivo allowing breakdown of the multimeric particles following administration to the human or animal body.

Preferably the linker groups comprise at least one such cleavable group. Particularly preferred cleavable groups include peptide bonds and ester linkages, as well as mixed acetal linkages, particularly between rings of a di- or higher polysaccharide. Other suitable cleavable groups include those known to a person skilled in the art, for example ether linkages. Thus, preferred cleavable groups include groups of formula —NR—CO— where R is an amino acid residue, and —CO—O— groups, as well as acetal groups. Examples of linker groups that are particularly useful in the present invention include linker groups containing proteins, peptides, polysaccharides and other carbohydrates, ester, amide, acetal, ether and phosphate linkages, for example DNA. Furthermore, each linker group can comprise more than one cleavable group. If more than one cleavable group is present, the groups may be the same or different.

Preferably the cleavable group is enzymatically cleavable. Enzymatic cleaving has particular relevance where the linker group comprises a peptide sequence. The exact nature of the peptide sequence can be manipulated in order to manipulate the ease and specificity of degradation. Enzymatic cleaving also allows multimeric particles having a particular peptide-containing linker group to remain intact during progress through a patient until it reaches a part of the body where the relevant enzyme is found. Accordingly, choice of linker group can be used to control the region of the body in which cleaving occurs and, therefore, at which breakdown of the multimeric particle occurs.

Example 2 hereinbelow describes the production of multimeric particles with a thrombin cleavage site. The multimeric particles are degradable to the constituent metal-containing particles.

Accordingly, in one embodiment, the cleavable group is a group which is cleavable by the enzyme thrombin. Thus, the linker groups may comprise at least one group which is cleavable by thrombin. Typically, the group which is cleavable by thrombin is a peptide which comprises the known thrombin cleavage sequence Phe-Val-Arg. Typically, the peptide further comprises amino acid spacer units, for instance glycine spacer units, either side of the cleavage sequence Phe-Val-Arg.

In the case of peptide bonds, multimeric particles having peptide linker groups are particularly useful for targeting of the tissue plasminogen activator (tPA) binding site. In the case of fibronectin and collagen linking groups, as an example, these are useful in imaging of regions where collagenase activity is present, for example in sites of tumour metastasis or sites of active inflammation. At such sites degradation of the large to small particles would give rise to improved local contrast.

In addition to the functionalisation which is present in, or is introduced into, the coatings and which allows binding to the linker groups, the metal-containing particles can be further functionalised in order to provide targeting moieties. The targeting moieties can be selected to target the conjugates to a selected cell type or tissue. The targeting moieties can be present on the metal-containing particles (e.g. bonded to the dextran coat or a dextran-coated iron oxide particle) and/or can be present on the linker groups.

Suitable targeting moieties include sugars, antibodies, peptides, lipids, lectins and signalling proteins, as well as and other moieties such as small molecules capable of targeting a desired cell type or tissue.

Preferred sugar targeting moieties include monosaccharides and oligosaccharides, and are selected to bind a cell surface receptor such as the selectin and lectin receptors. In a particularly preferred embodiment, the targeting moiety specifically targets a selectin or lectin, preferably a selectin, and most preferably selectin E or selectin P or both.

The targeting moiety is preferably a sugar. The targeting moiety may be a monosaccharide, but is more preferably an oligosaccharide. Monosaccharides can include fused bicyclic units. When oligosaccharides are employed, these comprise from 2 to 15 saccharide units, more preferably from 2 to 10 saccharide units, for example from 2 to 6 saccharide units. Preferred oligosaccharides include those having 2 saccharide units (disaccharides), 3 saccharide units (trisaccharides) or 4 saccharide units (tetrasaccharides). The saccharide units used in the oligosaccharides are chosen depending upon the target to which the conjugate is aimed. However, suitable building blocks which make up the oligosaccharides include hexoses such as glucose, galactose and mannose, deoxyhexoses such as fucose and rhamnose, and pentoses such as arabinose and xylose.

The saccharides used in the invention can be functionalised. For examples, one or more hydroxy groups on an unfunctionalised saccharide may be replaced by a group selected from hydrogen, halogen, mercapto, $C_{1-6}$ alkoxy, $C_{1-6}$ alkylthio, —COOR' where R' is hydrogen or a $C_{1-6}$ alkyl group, amino, $C_{1-6}$ alkylamino, di($C_{1-6}$)alkylamino, $C_{1-6}$ acetylamino, di($C_{1-6}$)acetylamino and phosphate. Suitable phosphate groups include those of formula —O—PO(OH)$_2$. When the substituent is halogen, it is preferably fluorine. When the substituent is an alkoxy group it is preferably methoxy or ethoxy. When the substituent is —COOR', preferably R' is hydrogen, methyl or ethyl. When the substituent is a C$_{1-6}$ acetylamino group it is preferably a group of formula —NH-COR' wherein R' is a C$_{1-6}$ alkyl group, preferably methyl or ethyl.

Thus, suitable saccharide units which can be present either alone or in oligosaccharides include monosaccharides such as GalNAc (N-acetyl galactosamine), GalUA (galacturonic acid), GlcNAc (N-acetyl glucosamine), GlcUA (glucuronic acid), IdUA (iduronic acid) and sialic acids such as NANA (neuraminic acid).

Particularly preferred saccharide units include N-acetyl glucosamine, fucose, galactose and sialic acid (Sia). When the targeting moiety is an oligosaccharide, the monosaccharides which comprise the oligosaccharide are the same or different. For example, targeting moieties may be Sialyl Lewis X (GlcNAc(-Fuc)-Gal-Sia), Lewis X (GlcNAc(-Fuc)-Gal), GlcNAc-Gal and GlcNac-Gal-Sia.

Preferred antibody targeting moieties include monoclonal and polyclonal antibodies. For examples immunoglobulins can be covalently linked to a dextran coating of a metal-containing particle using a periodate-oxidation/borohydride-reduction method, which, through the formation of Schiff bases as intermediates, covalently links the amine (lysine) groups of a monoclonal antibody to alcohol groups of the dextran coat. Such functionalisation of metal-containing particles is known in the art, and has been used previously to conjugate polyclonal IgG for the detection of induced inflammation, the monoclonal antibody fragments for the specific visualization of myocardial infarction, to intact monoclonal antibodies for immunospecific detection of intracranial small cell lung carcinoma, intracellular adhesion molecule (ICAM-1) gene expression on transfected cell lines and oligodendrocyte progenitors, and to synaptotagmin I for detection of apoptotic tumour cells. Other methods are also known for attaching antibodies to the metal-containing particles, such as through glutaraldehyde crosslinking, complexing through ultrasonication, using biotinstreptavidin system and amine-sulfhydryl group linkage.

The targeting moieties may be selected to target a selected receptor depending on the diagnosis or imaging that is required. For example, the targeting to selectin using Sialyl Lewis X allows visualisation of areas of inflammation. The selectin receptor to which Sialyl Lewis X binds is up-regulated on the epithelium during inflammation. Thus targeting to this selectin can show areas of inflammation. Targeting to other lectins can be useful for example where such lectins are up-regulated in tumours.

For the avoidance of doubt, where an metal-containing particle used in the invention is conjugated to more than one targeting moiety, the targeting moieties may be the same or different.

In addition to the targeting moieties, the metal-containing particles can be further functionalised to provide additional properties, for example to improve solubility, phagocytosis, non-antigenicity or to act as in vivo lifetime modulators.

As an example, the particles can be further functionalised with polyethylene glycol (PEG) moieties or similar solubilising groups in order to improve solubility. Thus, the particles can be PEGylated. In addition or alternatively, the particles can be further functionalised by peptides containing RGD sequences and other opsonins (such as MFG-E8) in order to improve phagocytosis. Other exemplary functionalising groups will be known to the skilled person.

The multimeric particles of the invention can be formulated for use by combining in a formulation with a pharmaceutically acceptable excipient. The formulations are typically prepared following conventional methods and are administered in a pharmaceutically suitable form.

The dosages in which the formulations according to the invention are administered will vary according to the mode of use and the route of use, as well as to the requirements of the patient and the degree of contrast required, and also the region of the body to which the contrast agent is intended to image.

Solid oral forms of the formulations of the invention may contain, together with the multimeric particles themselves, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non toxic and pharmacologically inactive substances used in pharmaceutical formulations. Such formulations may be manufactured in known manner, for example, by means of mixing, granulating, tableting, sugar coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the conjugated particles of the invention, a pharmaceutically acceptable carrier, e.g. sterile water, olive oil, ethyl oleate, glycols, e.g. propylene glycol, and if desired, a suitable amount of lidocaine hydrochloride.

Solutions for injection or infusion may contain as carrier, for example, sterile water or preferably they may be in the form of sterile, aqueous, isotonic saline solutions. Most preferably the formulation comprises multimeric particles according to the invention and saline.

In liquid formulations, the multimeric particles can suitable be formulated to give a final concentration of around 10 to 100 mg iron/mkg, for example from 10 to 50 mg iron/mkg such as around 20 mg iron/mkg.

The multimeric particles according to the present invention can be used as contrast agents in methods of imaging. The agents of the present invention are particularly useful as contrast agents using magnetic resonance imaging (MRI). The agents can be delivered to the patient under investigation by any suitable route, but are typically provided by injection, usually intravenous injection. The agents of the present invention may cross the blood brain barrier and so may be particularly useful in the monitoring or diagnosis of conditions affecting the brain. In a preferred embodiment, the contrast agents are used in the monitoring and diagnosis of inflammation. The agents may also be useful, depending on the targeting moiety selected for the monitoring and diagnosis of tumours. Such agents will preferably target tumours.

In a particularly preferred embodiment according to the present invention, the agents are used in the monitoring and diagnosis of inflammation in the brain, and are particularly useful in the diagnosis of multiple sclerosis.

The contrast agents of the present invention can also be used to screen a patient for responsiveness to a particular drug before treatment with that drug is prescribed. In this embodiment, the contrast agent comprises multimeric particles of the invention attached by any suitable means to the therapeutic agent of interest. This contrast agent is administered to a patient for whom treatment with that particular therapeutic agent is being considered. The patient is then submitted to medical imaging, typically magnetic resonance imaging, to determine whether or not the therapeutic agent is present at the site of interest in the patient's body. An informed clinical decision can then be taken as to whether or not the treatment of that patient with that therapeutic agent is likely to be effective. This approach saves time and cost, and allows ineffective treatment regimens to be avoided.

Accordingly, in one embodiment the contrast agent of the present invention is for use in screening a patent for responsiveness to a therapeutic agent. Typically, the therapeutic agent is one which modifies or targets adhesion molecules on the vascular endothelium, or their ligands. For instance, the therapeutic agent may be beta-interferon.

When the imaging agents of the invention are administered (e.g. by bolus injection), the signal from the circulating agent begins to decay exponentially. At the same time, specific binding of the particles increases at the site to which the particles are targeted. When the signal from the bound particles exceeds the signal from the unbound particles, significant contrast over the background can be seen. The time taken for this contrast to emerge will depend on a number of factors, for example the nature of the targeting moieties, other functionalisation of the particles, the location to which the contrast agent is administered and/or targeted etc. In some instance, the best contrast can be obtained over a period of minutes to hours, for example around 1 hr after administration.

The improved contrast properties of the particles of the invention can be seen by comparing with known administration of small non-multimeric particles. In such cases, the signal from the bound particles never exceeds the concentration in circulation sufficiently to give good contrast: in this case the signal is dependent solely upon the strength and speed of the receptor binding on the surface of the particle.

Processes:

The invention also provides a process for preparing the multimeric particles of the invention, wherein the process comprises:
  (a) providing a plurality of metal-containing particles and a plurality of linker group reactants; and
  (b) reacting said metal-containing particles and linker groups reactants in order to form a multimeric particle comprising metal-containing particles covalently bonded to one another by linker groups derived from said linker group reactants;
wherein at least a portion of said linker groups are cleavable. As used herein, linker group reactants are groups which, when reacted with the metal-containing particles, provide the linker groups. Typically they comprise said linker groups with reactive functional groups which are capable of bonding to the metal-containing particles.

The metal-containing particles and linker group reactants are preferably reacted under conditions sufficient to promote the reaction and/or in the presence of additional materials such as catalysts and cross-linking agents which promote the reaction. The skilled person will be able to choose suitable conditions and additional materials for use in conjunction with a range of metal-containing particles and linker group reactants.

An exemplary process to prepare multimeric particles according to the present invention is as follows:

Example 1

Preparation of Multimeric Particles

Amine-functionalised particles (20-40 nm) were stirred with succinic anhydride for 24 h and purified by magnetic affinity. The particles were concentrated by vivaspin and reacted with 2-ethoxy-1-ethoxycarbonyl-1,2-dihydroquinoline (EEDQ). The very concentrated solution of these activated particles was vigorously mixed with a solution of bovine serum albumin in water (100 mg/mL). Resulting particles were retrieved by magnetic affinity purification and size-selected using ultrafiltration. Laser scattering analysis indicated the resultant particulate solution to be in the 0.5 to 1 μm size range.

This exemplary process can be readily modified in order to produce other types of multimeric particles within the scope of the invention. For example, where the linker groups are or contain peptides, the particles could be prepared by mixing the relevant peptide or peptides with amine-terminated dextran-coated iron oxide particles and an agent to promote the reaction of these reactants and cause cross-linking of the metal-containing particles. In this example, succinic anhydride would be an appropriate reagent. The dextran-coated iron oxide particles could of course be substituted with other suitable metal-containing particles.

In another embodiment, where the linker groups are or contain polysaccharides, then the particles can be prepared by using glutaraldehyde or a di-bromo species or epichlorohydrin as the agent to facilitate cross-linking of the particles and preparation of the multimeric particles of the invention.

In effect, the skilled person simply needs to choose an appropriate metal-containing particle for the desired purpose, then choose a linker group which will is cleavable under the desired conditions, and react these in the presence of a reagent and/or under conditions such as to promote formation of the multimeric particles.

Example 2

Preparation of Multimeric Particles with a Thrombin Cleavage Site

Multimeric particles with a thrombin cleavage site have been generated; the multimeric particles are degradable to their constituent iron-containing particles.

Modification of Particles with Peptide

In order to create a linkable particle scaffold, the particles had to be modified with a thrombin-cleavable peptide. The peptide employed, whose sequence is shown below, contained (i) glycine spacer units, (ii) the known thrombin cleavage sequence Phe-Val-Arg in the middle, and (iii) a C-terminal glutamic acid allowing for facile linkage through the sidechain using a rink amide resin.

Fmoc-Gly-Gly-Gly-Gly-Phe-Val-Arg-Gly-Gly-Gly-Glu-NHAc

This peptide was synthesised on a 1 g scale on an automated peptide synthesiser.

Cross-Linking of the Particles

Peptide couplings are most readily performed in DMF using, for example, HOBT and DIC as coupling agents. It was thus explored whether the particles were stable in this medium and whether or not peptide modification could be performed.

In order to assess the modification levels after modification the Fmoc moiety was left at the N-terminus of the peptide allowing for the determination of incorporation by Fmoc-numbering. An incorporation level of 61 nmol/mg of iron was determined, which corresponds to 17% of all amine-groups being modified.

Figure 1:
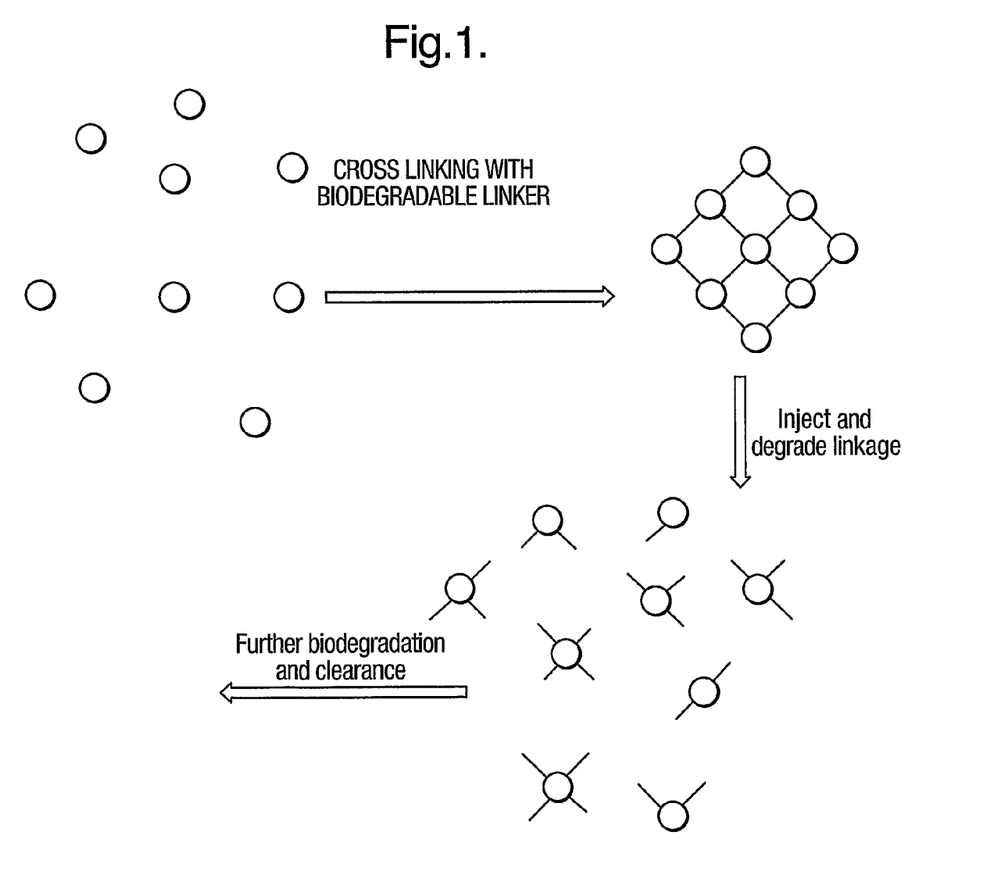
Figure 2:
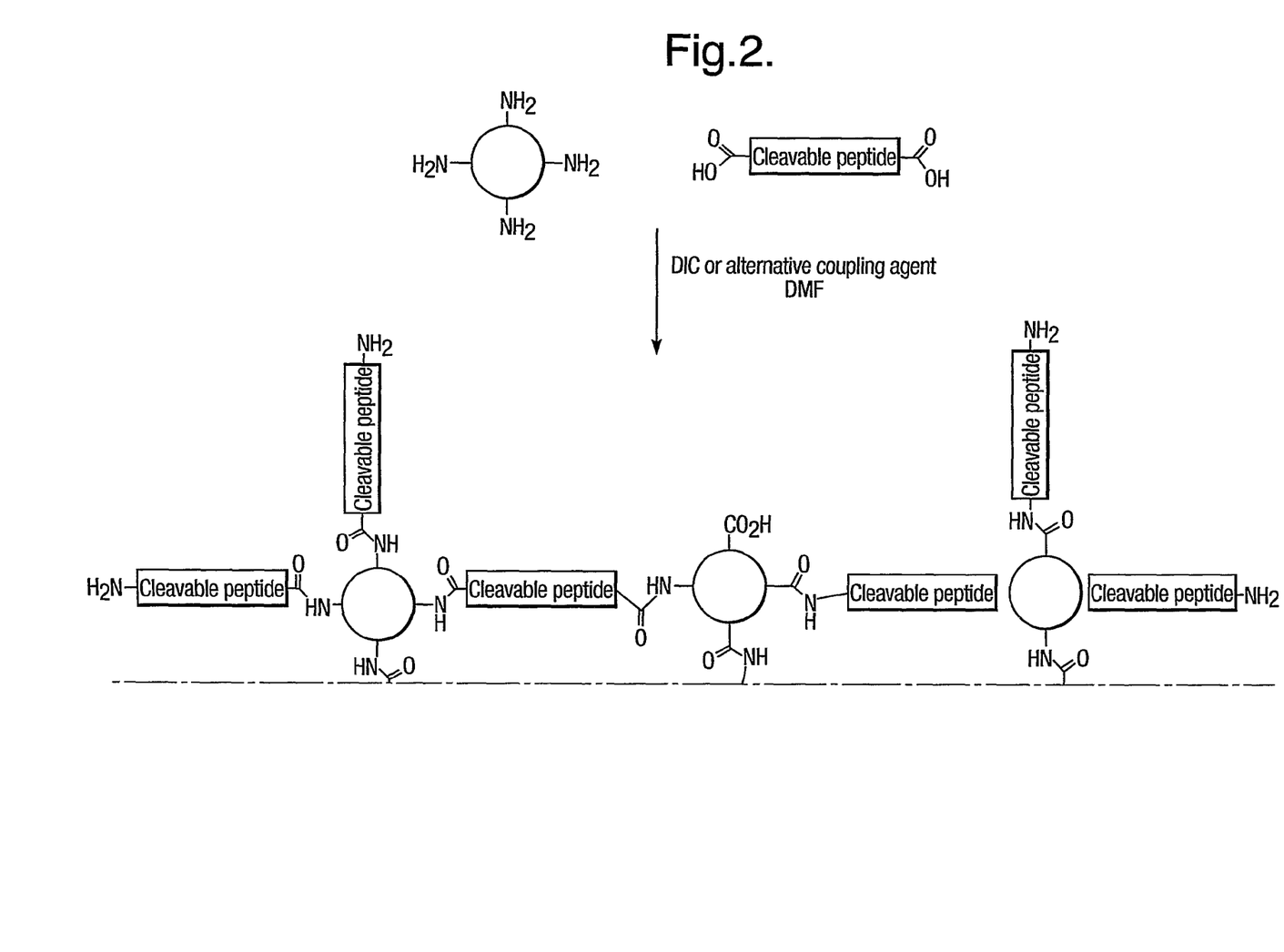
FIG. 2 is a schematic diagram of a cross linking strategy using a doubly functional linker. It illustrates the reaction between amino-functionalised metal-containing particles and carboxylic-acid-functionalised cleavable linkers to form multimeric particles by homodimeric coupling.
Figure 3:
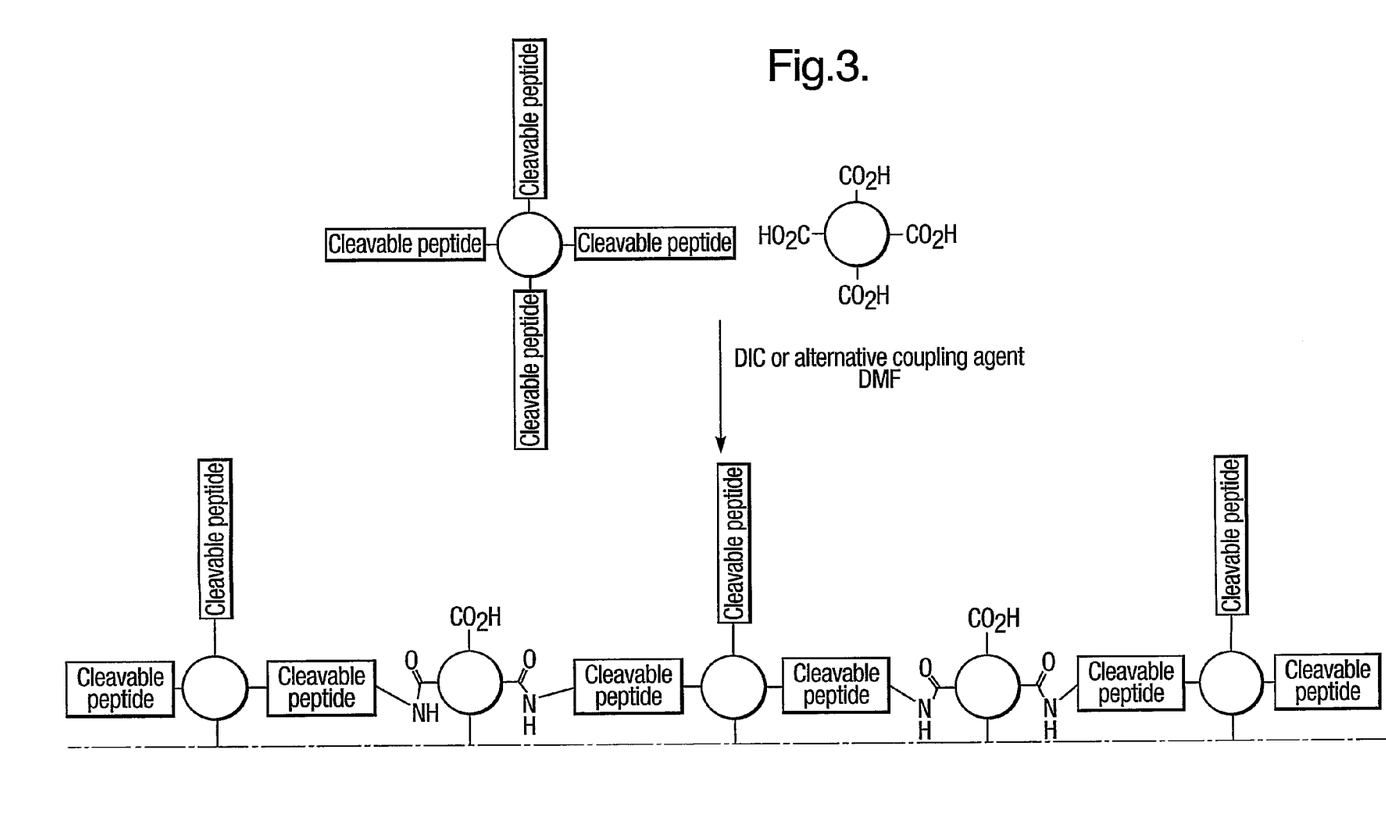
FIG. 3 is a schematic illustration of cross-linking based on two types of metal-containing particles (as used in Example 2): carboxylate-terminated succinic-anhydride-modified particles and amino-terminated peptide-modified particles. Such cross-linking allows for control over size by varying the ratio of DIC-activated carboxylate-terminated particles.
Figure 4:
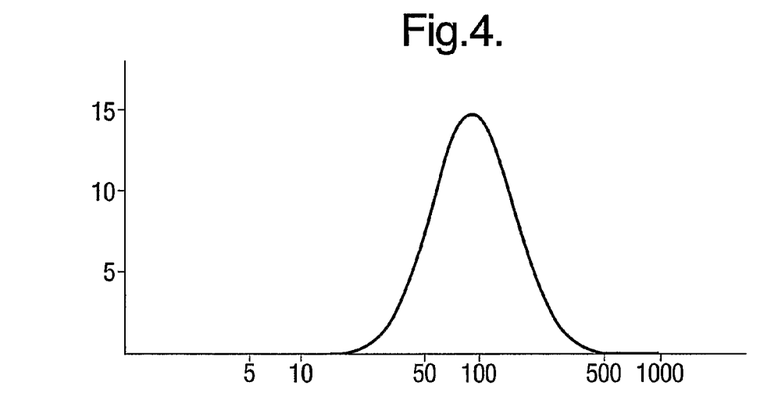
FIG. 4 is a graph showing the particle size distribution of the peptide-modified metal-containing particles used as a reactant in the cross-linking reaction of Example 2 (schematically illustrated in FIG. 3). The x axis represents particle diameter in units of nm and the y axis represents % in class. The particle size of the peptide-modified starting material is shown to be 89.4 nm.
Figure 5:
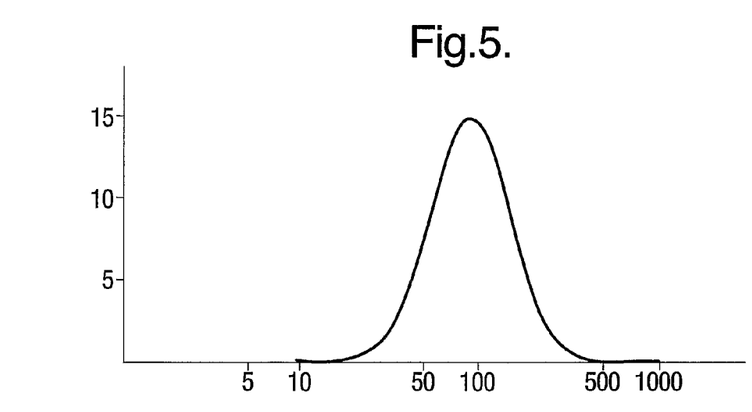
FIG. 5 is a graph showing the particle size distribution of the succinic-anhydride-modified metal-containing particles used as a reactant in the cross-linking reaction of Example 2 (schematically illustrated in FIG. 3). The x axis represents particle diameter in units of nm and the y axis represents % in class. The particle size of the succinic-anhydride-modified starting material is shown to be 86.3 nm.

In order to get some control over size distribution, it was decided to use 2 different types of particles (as shown schematically in FIG. 3), rather than to opt for a homodimeric coupling strategy (as shown schematically in FIG. 2). In order to achieve this, particles of a second batch were modified with succinic anhydride to provide a carboxylic acid handle (the particles remained the same size after modification, as shown in FIG. 5); this would allow for selective reaction with the amino-terminus of the peptide-modified particles.

Figure 6:
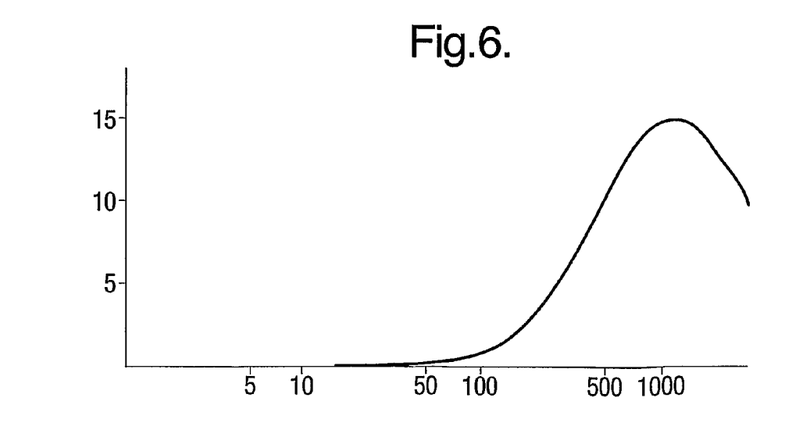
FIG. 6 is a graph showing the particle size distribution of the multimeric particle product obtained from the cross linking reaction of Example 2 (schematically illustrated in FIG. 3) between succinic-anhydride-modified particles and peptide-modified particles. The x axis represents particle diameter in units of nm and the y axis represents % in class. The particle size of the multimeric particle product is shown to be 1.7 µm.

By varying the ratio of the particles, some control can be exerted over the size distribution of the product particles. By using a 4:1 ratio of peptide vs carboxylic acid particles, a mean particle size distribution of 1.7 μm was achieved (see FIG. 6). This can be further narrowed using specific centrifugation protocols as well as size-cut off membranes.

which will be known to the skilled person. Once particular method is reductive amination. Other coupling methods are, of course, available, for example click chemistry, Staudinger ligations, peptidic couplings, Suzuki cross couplings and any other suitable coupling method. Any of the cross linking methods can be used for coupling in a separate step after the multimeric particles have been formed.

The metal-containing particles used in the invention are often commercially available. If further functionalisation is required, for example to add targeting moieties such as sugars, this can be achieved using processes known in the art. In particular, with regard to the specific instance of functionalisation of the metal-containing particles with saccharides, this can be achieved using a protected thio-cyanomethyl intermediate and converting this to a 2-methyl-2-imido-linker (IME) system in order for subsequent conjugation to take place.

It is possible to react a protected monosaccharide in an excess of sodium methoxide and methanol in order to deprotect the monosaccharide and simultaneously generate the IME system, hence activating the linker. This is shown along the top line of Scheme 1 below.

Scheme 1:

In the exemplary processes described above, the resulting multimeric particles do not contain further functionalisation (e.g. targeting moieties). Targeting moieties can, however, be introduced after formation of the multimeric particles. For example, the targeting moieties can be introduced onto remaining free amine groups on an amine-functionalised dextran-coated iron oxide particle or CLIO, or onto linker groups such as free amine groups on protein linker groups.

Alternatively, targeting moieties can be introduced prior to formation of the multimeric particles. For example, they can be introduced onto the initial metal-containing particles or the reactants used to form the linker groups. In the latter case, this may, however, be less preferred because it may increase wastage of the targeting moiety materials. Regardless of when in the process of manufacture they are introduced, targeting moieties can be introduced by a number of suitable means However, the product of this reaction is short lived, and it is furthermore currently difficult to add further targeting moieties onto this compound either before or after conjugation to an iron containing colloidal particle.

However, the process can be improved by uncoupling the deprotection and activation steps of the above reaction. Thus, the thio-cyanomethyl intermediate can be deprotected first, then subsequently extended by the addition of further targeting moieties without the IME system being generated. For example, in Scheme 1 above, by using a catalytic amount of sodium methoxide and methanol, the AcO groups on the starting material can be deprotected by conversion to hydroxy groups, without the IME system being generated. The deprotected but unactivated compound can then be extended by the addition of a further targeting moiety and finally the intermediate can be activated by the conversion of the thio-cyanomethyl group to the IME system. This IME-terminated compound can then be conjugated to a metal-containing particle, for example an iron-containing particle which comprises a dextran coat.

In the case of metal-containing particles conjugated to sugars, the number of further targeting moieties added to the starting material can vary. However, it is preferred that between one and four further moieties are added, more preferably one or two, and most preferably just one. These further carbohydrate-based moieties are preferably saccharides, most preferably monosaccharides. Furthermore, the number of targeting groups present in the starting material can vary, although preferably the starting material contains one or two, more preferably one, saccharide group. Accordingly, it is preferred that a monosaccharide is reacted as shown above in Scheme 1 by the addition of a further monosaccharide in order to produce an IME-terminated disaccharide which can subsequently be used to prepare the conjugates according to the invention.

The invention claimed is:

1. A multimeric particle comprising metal-containing particles covalently bonded to one another by linker groups wherein at least a portion of said linker groups are cleavable, wherein the multimeric particle is from more than 500 nm to 2 μm in diameter and wherein the average particle diameter of said metal-containing particles is from 1 nm to 200 nm.

2. A multimeric particle as claimed in claim 1 wherein at least a portion of the linker groups are enzymatically cleavable.

3. A multimeric particle as claimed in claim 1 wherein at least a portion of the linker groups are cleavable in vivo.

4. A multimeric particle as claimed in claim 1 wherein the linker groups comprise protein, peptide, polysaccharide, carbohydrate, ester, amide, ether and/or phosphate linkages.

5. A multimeric particle as claimed in claim 1 wherein the metal-containing particles comprise a metal or metal oxide core at least partially covered with a coating, said coating being covalently bonded to one or more linker groups.

6. A multimeric particle as claimed in claim 1 wherein the metal-containing particles are iron-containing particles.

7. A multimeric particle as claimed in claim 6 wherein the iron-containing particles comprise iron oxide.

8. A multimeric particle as claimed in claim 1 which is paramagnetic.

9. A multimeric particle as claimed in claim 1 which is superparamagnetic.

10. A contrast agent comprising a multimeric particle as claimed in claim 1.

11. A contrast agent as claimed in claim 10 which further comprises a pharmaceutically acceptable excipient.

* * * * *